(12) United States Patent
Yim

(10) Patent No.: US 7,647,934 B2
(45) Date of Patent: Jan. 19, 2010

(54) FLOSSER DEVICE

(75) Inventor: Wingchun Yim, Hong Kong (HK)

(73) Assignee: Conxept Limited, Hong Kong (HK)

( * ) Notice: Subject to any disclaimer, the term of this patent is extended or adjusted under 35 U.S.C. 154(b) by 327 days.

(21) Appl. No.: 11/843,370

(22) Filed: Aug. 22, 2007

(65) Prior Publication Data

US 2008/0047574 A1 Feb. 28, 2008

(30) Foreign Application Priority Data

Aug. 23, 2006 (CN) .................... 2006 2 0129478 U

(51) Int. Cl.
*A61C 15/00* (2006.01)
(52) U.S. Cl. ...................................... 132/323
(58) Field of Classification Search ............. 132/323, 132/329, 326, 327, 309, 310; 15/114.1, 144.2, 15/172
See application file for complete search history.

(56) References Cited

U.S. PATENT DOCUMENTS

| 3,927,686 A | 12/1975 | Zambito |
| 2003/0098037 A1 | 5/2003 | Dougan et al. |
| 2005/0092346 A1 * | 5/2005 | Gwen .................... 132/323 |
| 2009/0165814 A1 * | 7/2009 | Welt et al. ............. 132/323 |

FOREIGN PATENT DOCUMENTS

| CN | 1686060 | 10/2005 |
| EP | 1 449 495 A2 | 8/2004 |

* cited by examiner

*Primary Examiner*—Robyn Doan
*Assistant Examiner*—Rachel R Steitz
(74) *Attorney, Agent, or Firm*—Fitch, Even, Tabin & Flannery

(57) ABSTRACT

The present invention relates to a dental cleaning device, particularly to a flosser device for cleaning teeth gaps. The flosser device according to the present invention removes food particles from different tooth gaps by mounting the flosser element to the flosser element longitudinal connecting slot and the flosser element transverse connecting slot to adjust the position of the flosser. The flosser element base is disposed in the gradually narrowing flosser element connecting slots, so that the flosser element arms diverse outwardly to tension a length of flosser between the flosser element arms. Besides, the center of the flosser element connecting slot is hollow to form a base receiving hole so that the base press-release point projects through the base receiving hole out of the handle after the flosser element base is mounted on the flosser element connecting mechanism, and a user can draw out the flosser element by pressing the base press-release point for replacement.

8 Claims, 4 Drawing Sheets

FLOSSER DEVICE

TECHNICAL FIELD

The present invention relates to a dental cleaning device, particularly to a flosser device for cleaning teeth gaps.

BACKGROUND

Currently, there are many methods of cleaning tooth gaps that range from toothpick to flossers which can all substantially realize the cleaning purpose. A toothpick is an elongated device with a pointed end, whereby the waste and food particles are removed by moving the pointed end through the tooth gaps. A flosser is a linear object, whereby waste and food particles in the tooth gaps are removed by putting the flosser through the tooth gaps when tightly griping two ends of the flosser. Yet, the above methods are difficult to implement so that inconvenience is caused to a user.

There are a lot of known technologies in the market targeted at the above problems. One is the US 2003/0098037 entitled ("Dental Floss Device" published on May 29, 2003, wherein a user can tightly grip the handle of the floss device in cooperation with the floss element on the top, such that the floss element goes into the oral cavity to remove food particles in tooth gaps. Besides, only a small length of floss needs to be used on the floss element to achieve the same effect. But, the above floss element can only be assembled to the top of the handle in horizontal direction so that a user cannot adjust the direction of the floss according to the configuration of the oral cavity to remove food particles in the gaps between different teeth. The problem of inconvenience cannot be totally solved.

In view of the problem in the above device, another prior art is US 2005/0092346 entitled "Flosser apparatus with Detachable and Adjustable Floss Element" on May 5, 2005. The flosser apparatus can not only achieve the above effect but also solve the shortcoming that the floss element can only be assembled to the top of the handle in horizontal direction. Its cross-shaped floss element base cooperates with cross-shaped floss element connecting slot to adjust the direction of the floss element so that a user can adjust the direction of the floss according to the structure of the oral cavity to remove food particles in the gaps between different teeth. On the other hand, the configuration of the floss element base cooperates with the configuration besides the floss element connecting slot to cause a pressing force to allow the floss element arms to open to tension a length of floss between the floss element arms for ease of a user's use. However, the design thereof utilizes a third type of lever such as used in forceps, roasting clamps, chopsticks, that is, the point of force application is between the tension points and the pivot point, the pivot point is at the bottom of the floss element, and the point of force application is at the bottom of the floss element arms in the middle of the floss element. Besides, the positions where the top portions of the floss element open the floss are the tension points. The point of force application of this kind of lever is sure to be nearer to the pivot point than the tension points. So the apparatus requires a lot of user's force so that it is not desirable in opening the floss element arms. Moreover, after the floss element is mounted onto the floss element connecting slot, the floss element arms be detached for replacement purpose. The sole method is to firstly tightly grip the floss element arms, then draw hard. In this manner, the floss element arms are easily broken. The apparatus is not convenient in use, so the above problems are not completely solved.

SUMMARY OF THE INVENTION

In view of the above problems, an object of the present invention is to solve the problems of the above apparatuses and to provide a flosser device for removing food particles in gaps between different teeth, wherein the food particles in the gaps between different teeth can be removed by adjusting the direction of a flosser element, besides, special flosser element base structure cooperates with the structure nearby a flosser element connecting slot so that the flosser element can pull the floss more tightly and the flosser element can be more easily drawn out from a handle.

To achieve the above object, the present invention provides a flosser device for cleaning tooth gaps, comprising a handle including an upper portion and a lower portion respectively used as a handgrip of a gripping portion and a flosser element connecting mechanism at the top of the handle for fixing a flosser element; a flosser element mounted on the flosser element connecting mechanism and consisting of an upper portion being flosser element arms which top portion is fixed with a flosser and a lower portion being a flosser element base, the flosser element base being mounted in the flosser element connecting mechanism to form the flosser device, characterized in that the flosser element connecting mechanism at the top of the handle is provided with flosser element connecting slots, the center of the connecting mechanism is hollow to form a base receiving hole; the flosser element extends upwardly from the flosser element base to the top portion thereof to form flosser element arms to connect the flosser; the bottoms of the flosser element arms are connected to the top portion of the flosser element base and extend downwardly apart from the flosser element base to form flosser element arm hanging edges which is at a distance apart from the flosser element base, the flosser element connecting slots apply pressure to the flosser element arm hanging edge to pull the flosser element arms apart from each other to tension the flosser; a downwardly projecting base press-release point is provided at the bottom of the body of the base so that the flosser element base, after being mounted onto the flosser element connecting mechanism, runs through the base receiving hole to project out of the handle.

The flosser device according to the present invention removes food particles from different tooth gaps by mounting the flosser element to the flosser element connecting slots in different directions to adjust the position of the flosser; a special flosser element base structure is used to cooperate with the structure nearby the flosser element connecting slots; the theory of the first kind of lever is utilized so that the pivot point is between the point of force application and the tension points to effectively open the flosser element arms to tension a length of flosser between the flosser element arms; moreover, since the base press-release point projects out of the handle after the flosser element base is mounted on the flosser element connecting mechanism, a user can draw out the flosser element by pressing the base press-release point for replacement. In this manner, the above problems are solved.

BRIEF DESCRIPTION OF ACCOMPANYING DRAWINGS

PREFERRED EMBODIMENTS

Figure 1:
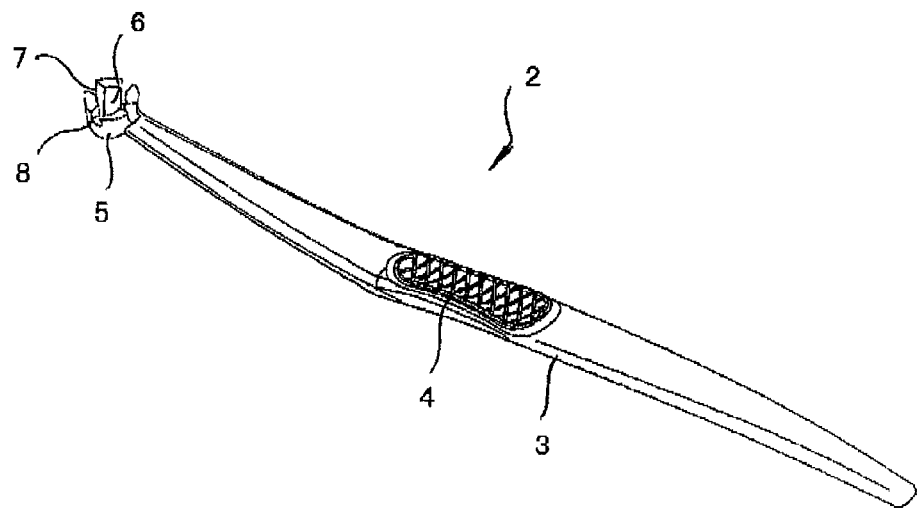
FIG. 1 is a perspective view of the handle of the flosser device according to the present invention.
Figure 2:
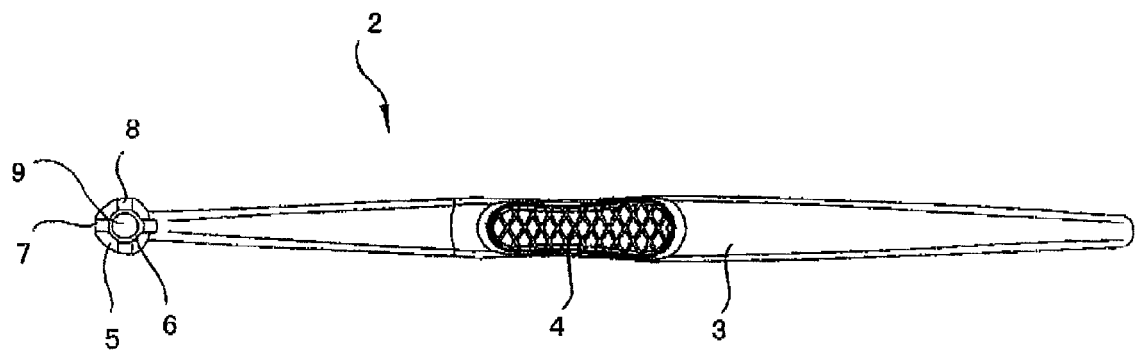
FIG. 2 is a top view of the handle of the flosser device according to the present invention.
Figure 3:
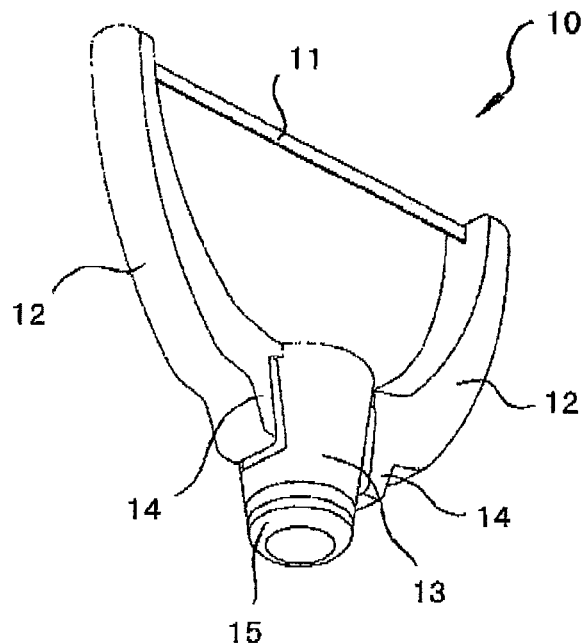
FIG. 3 is a perspective view of the flosser element mounted on the handle as shown in FIG. 1.

Firstly referring to FIGS. 1 and 2, the two figures show two views of a handle 2 of a flosser device 1 according to the present invention. The handle 2 comprises an upper portion used as a handgrip 3 for gripping, and a lower portion, i.e., a flosser element connecting mechanism 5 at the top of the handgrip for fixing a flosser element 10 (as shown in FIG. 3). The central portion of the handgrip 3 is indented to form a finger press location 4, which is provided with projecting net-like textures for facilitating a user tightly holding the handle 2 and controlling the flosser device 1. In addition, the flosser element connecting mechanism 5 is provided with flosser element connecting slots 6 at the tip of the handle 2. The flosser element connecting slots 6 are divided into a flosser element longitudinal connecting slot 7 and a flosser element transverse connecting slot 8 to assist the flosser element 10 (as shown in FIG. 3) in being longitudinally or transversely mounted into the flosser element connecting mechanism 5 so as to form the flosser device 1. The flosser element connecting slots 6 extend downwardly and narrows inwardly, and form a hollow base receiving hole 9 at the center thereof.

Figure 4:
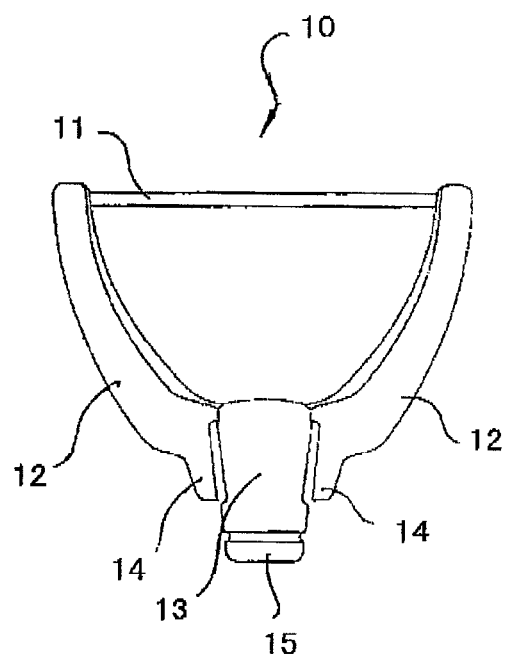
FIG. 4 is a front view of the flosser element shown in FIG. 3.
Figure 5:
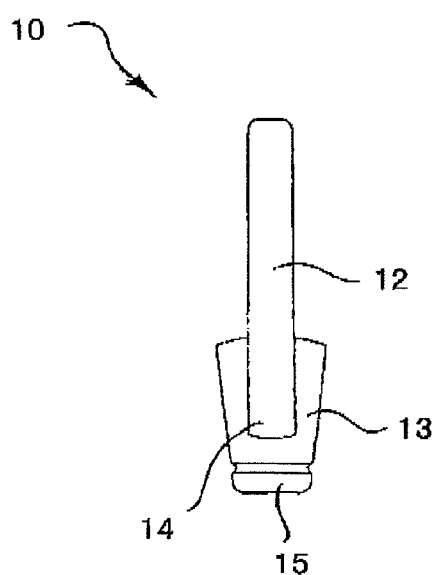
FIG. 5 is a side view of the flosser element shown in FIG. 3.

FIGS. 3-5 show a flosser element 10 capable of being mounted on the handle 2. The flosser element 10 is divided into an upper portion, i.e., flosser element arms 12 for fixing a flosser 11 at the top, and a lower portion, i.e., a flosser element base 13 at the bottom thereof. The flosser element base 13 can be mounted on the flosser element connecting mechanism 5 to form the flosser device 1. The flosser element arms 12 are arcuate and extend upwardly from the flosser element base 13, and the bottom of the flosser element arms is connected to the top of the flosser element base 13 and then extends downwardly apart from the flosser element base 13 to form a flosser element arm hanging edge 14. Said flosser element arm hanging edge 14 extends downwardly parallel to the body of the base 13 and remains a distance from the flosser element base 13, so that after the flosser element base is mounted on the flosser element connecting mechanism 5, the flosser element connecting slots 6 applies pressure to the flosser element arm hanging edge 14 to pull the flosser element arms 12 apart from each other so as to pull the flosser 11 tight. On the other hand, a downwardly projecting base press-release point 15 is provided at the bottom of the body of the base 13, so that the flosser element base 13, after being mounted onto the flosser element connecting mechanism 5, runs through the base receiving hole 9 to project out of the handle 2.

Figure 6:
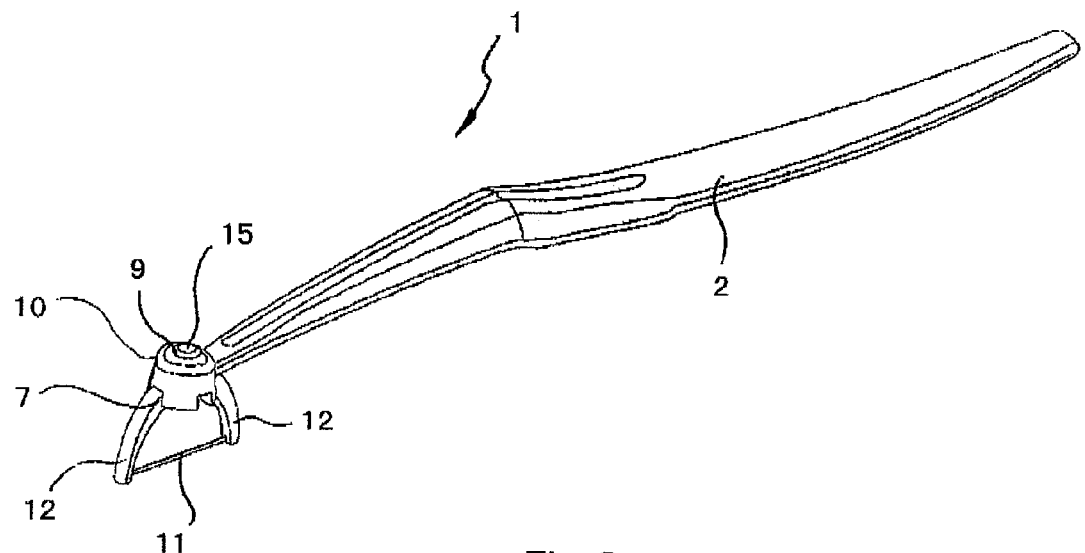
FIG. 6 is a perspective view of the back side of the flosser device formed by longitudinally mounting the flosser element on the handle.
Figure 7:
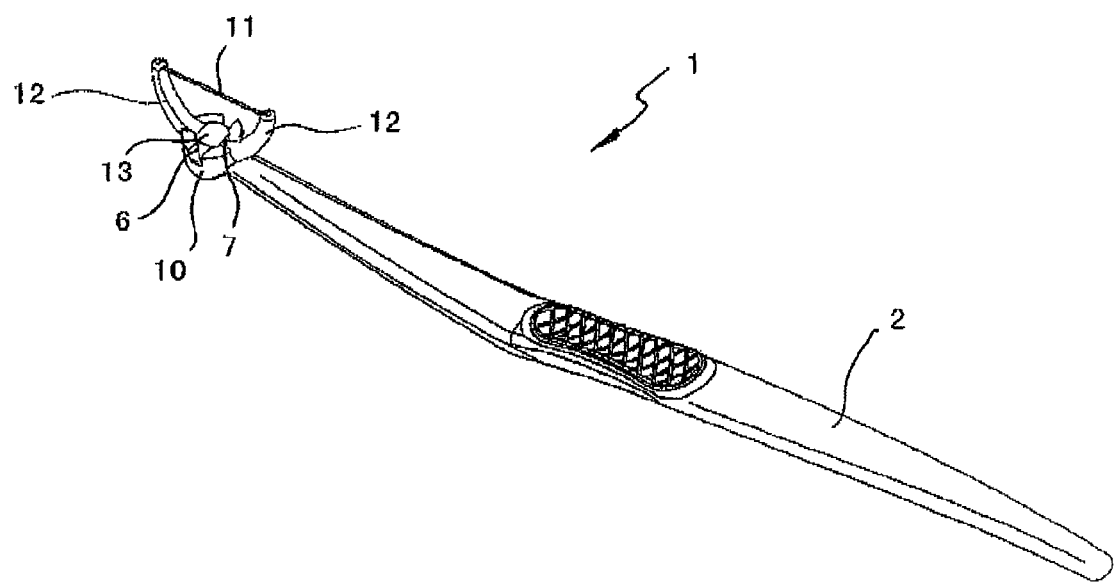
FIG. 7 is a perspective view of the front side of the flosser device of FIG. 6.

Now referring to FIGS. 6 and 7, said figures show an embodiment in which the flosser element 10 is longitudinally mounted on the handle 2 to form the flosser device 1. It can be seen from the figures that the handle 2 is parallel to the flosser element 10. The flosser element arms 12 are disposed in the flosser element longitudinal connecting slot 7 to facilitate a user cleaning food particles between the front row of teeth such as incisor tooth and canine tooth. Besides, the flosser element base 13 is disposed in the gradually narrowing flosser element connecting slots 6. The flosser element arm hanging edges 14 (as shown in FIGS. 3-5) are pressed inwardly as a point of force application, and the flosser element base 13 is used as a pivot point thereof so that the top ends of the flosser element arms 12 will open outwardly to tension a length of flosser 11 between the flosser element arms 12. Moreover, upon completion of installation, the user can draw out the flosser element 10 by pressing the base press-release point 15 projecting from the base receiving hole 9 out of the handle 2 for replacement.

Figure 8:
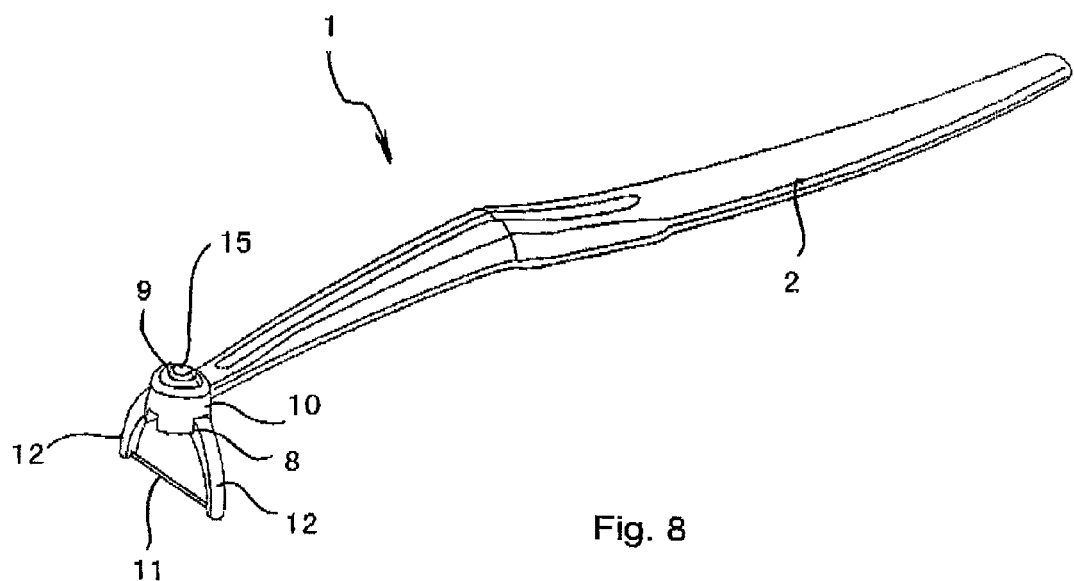
FIG. 8 is a perspective view of the back side of the flosser device formed by transversally mounting the flosser element on the handle.
Figure 9:
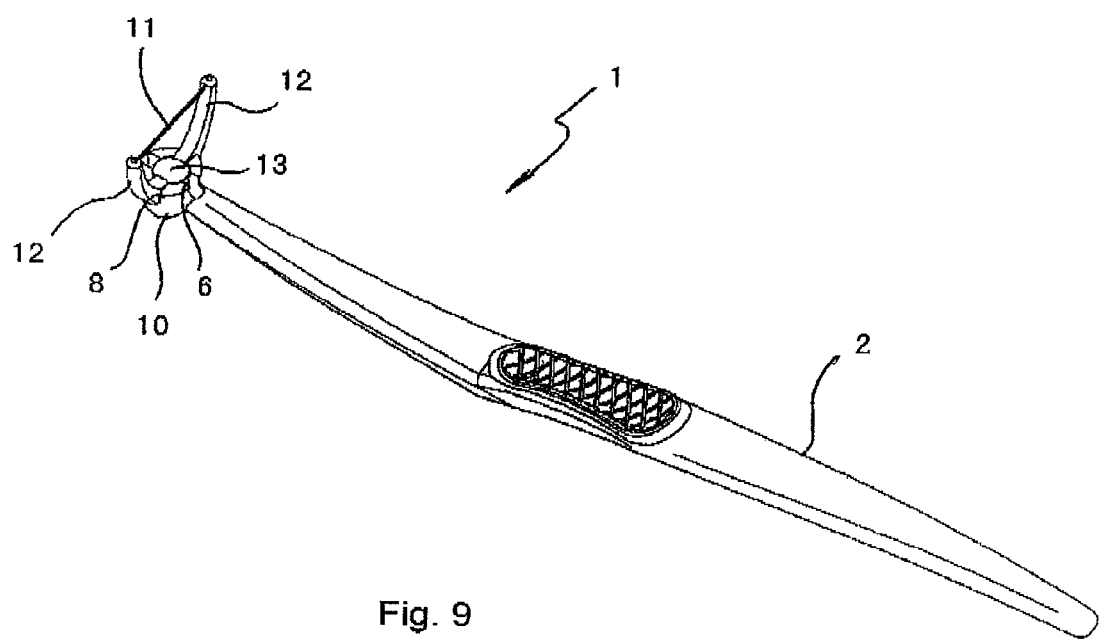
FIG. 9 is a perspective view of the front side of the flosser device of FIG. 8.

Finally, FIG. 8 and FIG. 9 respectively show an embodiment in which the handle 2 is transversely mounted on the flosser element 10 to form the flosser device 1. In said figures, the handle 2 is perpendicular to the flosser element 10, and the flosser element arms 12 are disposed in the flosser element transverse connecting slot 8 to assist a user in cleaning food particles between the rear row of teeth such as the molar tooth and the large molar tooth. Besides, the flosser element base 13 is likewise disposed in the gradually narrowing flosser element connecting slots 6 so that the flosser element arms 12 open outwardly to tension a length of flosser 11 between the flosser element arms 12. Moreover, the user can draw out the flosser element 10 by pressing the base press-release point 15 projecting from the base receiving hole 9 out of the handle 2 for replacement.

It is known from the above configuration that the flosser device 1 according to the present invention removes food particles from different tooth gaps by mounting the flosser element 10 to the flosser element longitudinal connecting slot 7 or the flosser element transverse connecting slot 8 to adjust the position of the flosser 11. The flosser element arm hanging edges 14 are used as a point of force application, the flosser element base 13 is used as a pivot point and the top ends of the flosser element arms 12 are used as tension points to form a first lever such that the flosser element arms 12 open outwardly to tension a length of flosser 11 between the flosser element arms 12. Moreover, since the base press-release point 15 projects out of the handle 12 after the flosser element base 13 is mounted on the flosser element connecting mechanism 5, the user can draw out the flosser element 10 by pressing the base press-release point 15 for replacement. In this manner, the above problems are solved.

The invention claimed is:

1. A flosser device for cleaning tooth gaps, comprising:
a handle including a handgrip and a flosser element connecting mechanism for fixing a flosser element at the top of the handle; and
a flosser element mounted on the flosser element connecting mechanism, which includes flosser element arms having a flosser fixed on the top portion thereof, and a flosser element base mountable in the flosser element connecting mechanism,
wherein, at the top of the handle, the flosser element connecting mechanism is provided with flosser element connecting slots, and the center of the connecting mechanism is hollow to form a base receiving hole;
the flosser element extends upwardly from the flosser element base to the top portion thereof to form flosser element arms for connecting a flosser, the bottoms of the flosser element arms are connected to the top portion of the flosser element base and extend downwardly apart from the flosser element base to form flosser element arm hanging edges which are at a distance apart from the flosser element base, the flosser element connecting slots apply pressure to the flosser element arm hanging edge to pull the flosser element arms apart from each other to tension the flosser;

a downwardly projecting base press-release point is provided at the bottom of the body of the base so that the flosser element base, after being mounted onto the flosser element connecting mechanism, runs through the base receiving hole to project out of the handle.

2. The flosser device according to claim 1, wherein the flosser element arms of the flosser device are arcuate and extend upwardly from the flosser element base.

3. The flosser device according to claim 1, wherein the flosser element connecting slots on the flosser element are divided into a flosser element longitudinal connecting slot and a flosser element transverse connecting slot to assist the flosser element in being longitudinally or transversely mounted into the flosser element connecting mechanism to form the flosser device.

4. The flosser device according to claim 2, wherein the flosser element connecting slots on the flosser element are divided into a flosser element longitudinal connecting slot and a flosser element transverse connecting slot to assist the flosser element in being longitudinally or transversely mounted into the flosser element connecting mechanism to form the flosser device.

5. The flosser device according to claim 3, wherein the flosser element connecting slots extend downwardly and narrow inwardly, so that can apply pressure to the flosser element arm hanging edges to pull the flosser element arms apart from each other to tension the flosser.

6. The flosser device according to claim 4, wherein the flosser element connecting slots extend downwardly and narrow inwardly, so that can apply pressure to the flosser element arm hanging edges to pull the flosser element arms apart from each other to tension the flosser.

7. The flosser device according to claim 5, wherein the flosser element arm hanging edges extend downwardly along and parallel to the body of the base.

8. The flosser device according to claim 6, wherein the flosser element arm hanging edges extend downwardly along and parallel to the body of the base.

* * * * *